(12) United States Patent
Glumac

(10) Patent No.: US 11,711,658 B2
(45) Date of Patent: *Jul. 25, 2023

(54) IMPLANTABLE MIDDLE EAR TRANSDUCER HAVING DIAGNOSTIC DETECTION SENSOR

(71) Applicant: Envoy Medical Corporation, White Bear Lake, MN (US)

(72) Inventor: Daniel E. Glumac, White Bear Lake, MN (US)

(73) Assignee: Envoy Medical Corporation, White Bear Lake, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/331,843

(22) Filed: May 27, 2021

(65) Prior Publication Data

US 2021/0289302 A1 Sep. 16, 2021

Related U.S. Application Data

(60) Continuation of application No. 15/385,731, filed on Dec. 20, 2016, now Pat. No. 11,051,116, which is a division of application No. 13/649,254, filed on Oct. 11, 2012, now Pat. No. 9,525,949.

(51) Int. Cl.
*H04R 25/00* (2006.01)
*A61F 2/18* (2006.01)

(52) U.S. Cl.
CPC .............. *H04R 25/60* (2013.01); *A61F 2/18* (2013.01); *H04R 25/00* (2013.01); *H04R 25/305* (2013.01); *H04R 25/554* (2013.01); *H04R 2225/57* (2019.05); *H04R 2225/67* (2013.01)

(58) Field of Classification Search
CPC ...... H04R 25/60; H04R 25/00; H04R 25/305; H04R 25/554; H04R 2225/57; H04R 2225/67; H04R 19/016; H04R 25/606
See application file for complete search history.

(56) References Cited

U.S. PATENT DOCUMENTS

| 4,729,366 | A | 3/1988 | Schaefer |
| 4,850,962 | A | 7/1989 | Schaefer |
| 8,270,647 | B2 | 9/2012 | Crawford et al. |
| 8,858,420 | B2 | 10/2014 | Elofsson |
| 11,051,116 | B2 * | 6/2021 | Glumac .............. H04R 25/554 |
| 2002/0026091 | A1 | 2/2002 | Leysieffer |
| 2003/0208099 | A1 | 11/2003 | Ball |

(Continued)

*Primary Examiner* — Samuel G Gilbert
(74) *Attorney, Agent, or Firm* — Fredrikson & Byron, P.A.

(57) ABSTRACT

Methods and devices for measuring vibration of an implanted driven vibrating elongate body coupled to a bone of the middle ear, for example using an accelerometer coupled to the vibrating body. The measured vibration can be taken during implantation and long again after implantation to check for possible decoupling, disease, or additionally impeded vibratory driving of the middle ear bone. An accelerometer signal can be converted to a displacement value and used to check for an under impeded or over impeded vibratory body. An implanted device can be used to periodically check the vibration of the vibratory body. Methods and devices can be used in conjunction with implanted devices which receive vibratory signals from a middle ear bone and use the signals to drive a disarticulated middle ear bone closer to the ear drum.

20 Claims, 6 Drawing Sheets

(56) References Cited

U.S. PATENT DOCUMENTS

2005/0096561 A1    5/2005   Conn et al.
2006/0178553 A1    8/2006   Neisz et al.
2007/0167671 A1    7/2007   Miller

* cited by examiner

IMPLANTABLE MIDDLE EAR TRANSDUCER HAVING DIAGNOSTIC DETECTION SENSOR

RELATED APPLICATIONS

This application is a continuation of U.S. patent application Ser. No. 15/385,731, filed Dec. 20, 2016, which is a divisional of U.S. patent application Ser. No. 13/649,254, filed Oct. 11, 2012, now U.S. Pat. No. 9,525,949. The contents of these applications are hereby incorporated by reference.

TECHNICAL FIELD

The present invention is related generally to implantable medical devices. More specifically, the present invention is related to implantable transducers, which can be used in partial middle ear implantable or total middle ear implantable hearing aid systems.

BACKGROUND

In an anatomically normal human hearing apparatus, sound waves, which represent acoustical energy, are directed into an ear canal by the outer ear (pinna) and impinge upon a tympanic membrane (eardrum) interposed at the terminus of the ear canal between the ear canal and the middle ear space. The pressure of the sound waves effect tympanic vibrations in the eardrum, which then become manifested as mechanical energy. The mechanical energy in the form of tympanic vibrations is communicated to the inner ear by a sequence of articulating bones located in the middle ear space, to which are generally referred as the ossicular chain. The ossicular chain must be intact if acoustical energy existing at the eardrum is to be conducted as mechanical energy to the inner ear. The ossicular chain includes three primary components: the malleus, the incus, and the stapes. The malleus includes respective manubrium, neck, and head portions. The manubrium of the malleus attaches to the tympanic membrane at a point known as the umbo. The head of the malleus, which is connected to the manubrium by the neck portion, articulates with one end of the incus, which provides a transmission path for the mechanical energy of induced vibrations from the malleus to the stapes. The stapes includes a capitulum portion connected to a footplate portion by means of support crura and is disposed in and against a membrane-covered opening to the inner ear, referred to as the oval window. The incus articulates the capitulum of the stapes to complete the mechanical transmission path.

Normally, tympanic vibrations are mechanically conducted through the malleus, incus, and stapes, to the oval window and to the inner ear (cochlea). These mechanical vibrations generate fluidic motion (transmitted as hydraulic energy) within the cochlea. Pressures generated in the cochlea by fluidic motion are accommodated by a second membrane-covered opening between the inner and middle ear, referred to as the round window. The cochlea translates the fluidic motion into neural impulses corresponding to sound perception as interpreted by the brain. However, various disorders of the tympanic membrane, ossicular chain and/or inner ear can occur to disrupt or impair normal hearing.

Hearing loss, which may be due to many different causes, is generally of two types, conductive and sensorineural. Of these types, conductive hearing loss occurs when the normal mechanical pathways for sound to reach the hair cells in the cochlea are impeded, for example, damage to the ossicles or the ossicular chain. Conductive hearing loss may often be helped by use of conventional hearing aids, which amplify sound so that acoustic information does reach the cochlea and the hair cells. In other cases, conductive hearing loss can be helped by the use of a middle ear implant, which essentially augments or bypasses the mechanical conduction of the ossicular chain. Some examples of such a middle ear implant can be found in U.S. Pat. Nos. 4,729,366 and 4,850,962 of Schaefer.

In some types of partial middle ear implantable (P-MEI) or total middle ear implantable (T-MEI) hearing aid systems, sounds produce mechanical vibrations within the ear which are converted by an electromechanical input transducer into electrical signals. These electrical signals are in turn amplified and applied to an electromechanical output transducer. The electromechanical output transducer causes an ossicular bone to vibrate in response to the applied amplified electrical signals, thereby improving hearing.

An electromechanical output transducer used for the purpose of causing an ossicular bone to vibrate may be mounted in or near the middle ear. The transducer, also known as a driver, is generally contained in a housing or enclosure, forming an assembly that facilitates the placement of the transducer within or near the middle ear.

In some previous designs, the output transducer assembly is coupled to some part of the middle ear and has its output portion typically coupled to the moving part of the ear, e.g. the stapes or another element in the ossicular chain. The output transducer, which may be piezoelectric, electromagnetic, electrostatic, or another mechanism, is mechanically coupled to the moving portion of the ear to be vibrated.

One method, for measuring the output vibration of the middle ear element to which the output transducer is coupled, is called Laser Doppler Velocimetry (LDV) or Laser Doppler Vibrometry. LDV typically uses a helium-neon laser, or something similar, and can be used to measure the Doppler shift between incident and reflected light from a vibrating surface such as a middle ear element or a middle ear transducer. This Doppler shift measurement can be used to calculate velocity, displacement, or acceleration of a middle ear element or middle ear transducer. LDV equipment can be expensive, and making LDV measurements in the middle ear can be difficult.

An elongate vibratory body, sometimes called a bimorph or bi-element, can be used to drive a bone in the middle ear. Often the bimorph will have two piezoelectric layers or bodies disposed on either side of a central conducting vane. When the top layer is caused to expand by application of an electric field, and the bottom layer is caused to contract by application of an electric field, the elongate body or bimorph will bend. Long after the implantation procedure, methods such as LDV obviously cannot be used due to the device residing within human tissue.

Undesirable changes may occur long after implantation. It is theoretically possible for the vibratory body to be decoupled from the middle ear bone. The growth of scar tissue, tumors, or other growth could impede the movement of the driven middle ear bone or other element and/or the vibrating body. Fluid buildup could also impede the vibrations. For these and other reasons, measuring the vibration of the driven middle ear bone and/or the vibratory body would also be desirable long after the initial surgery.

SUMMARY

Some embodiments of the present invention provide a method for treating a human, the method including: securing an accelerometer to a bone and/or tissue of the middle ear; and electronically and/or optically coupling the accelerometer to an implantable device disposed outside of the middle ear, where the accelerometer is secured to a vibrational device or is part of the vibrational device. In some methods the implantable device is implanted in a human skull. The securing is done during surgery in some such methods. One embodiment provides a method for sensing the vibrational driving of a middle ear bone by a vibrating element coupled to the middle ear bone, the vibrating element having an accelerometer coupled to the vibrating element and/or part of the vibrating element, the method including: coupling the vibrating element to the middle ear bone; and measuring a signal indicative of the acceleration from the accelerometer at a first time after the coupling. In one method the coupling is performed during a surgery and the first time measuring is performed during the surgery. The first time signal measuring includes receiving an electrical signal electronically coupled to the accelerometer and/or receiving an optical signal optically coupled to the accelerometer, in various embodiments. The first time signal measuring can include receiving an optical signal optically coupled to the accelerometer. The method can also include converting the signal indicative of acceleration to a value indicative of velocity, and/or converting the signal indicative of acceleration to a value indicative of displacement, in various embodiments. The first time measuring can be used to determine proper coupling of the vibrating element to the middle ear bone. The first time measuring can be performed after the surgery is complete and/or during surgery.

Some methods also include a second measuring of the signal indicative of the acceleration from the accelerometer at a second time after the coupling, in which the second measuring time is at least one month after the coupling, and further comprising comparing the first and second measuring time signals. The method can also include determining whether the vibrational driving is indicative of a vibrating element being uncoupled from the middle ear bone and/or include determining whether the vibrational driving is indicative of excessively impeded vibration of the middle ear bone.

The second measuring is compared to the first measuring to check for decoupling of the vibrator from the middle ear bone and/or to check for impeding of the vibration from the middle ear bone.

In various methods the accelerometer is a self-powered sensor, a piezoelectric device, an externally powered sensor, a capacitive device and/or combinations thereof.

Some embodiments of the present invention include a system for detecting vibration of a middle ear bone, the system including: an accelerometer electronically and/or optically coupled to an implantable electronic device, the implantable electronic device having implemented methods for converting accelerometer signals to displacement signals. In some systems the method includes electronically implemented instructions for converting the accelerometer signals to displacement signals. In various systems the accelerometer is a capacitive type sensor, the accelerometer is a piezoelectric type sensor, the accelerometer is electronically coupled to the implantable electronic device, the accelerometer is optically coupled to the implantable electronic device, and/or combinations thereof.

Embodiments of the present invention can include an implantable vibrational device for vibrating a bone of the middle ear, the device including: an elongate member having a first end region for securing to the skull and a second end region for coupling to a middle ear bone; an accelerometer secured to the elongate member second region; and a signal communication element for communicating information to a location outside of the elongate member where the signal communication element is coupled to the accelerometer. The signal communication element can include an electrical wire and/or an optical signal conductor in which the wire and/or optical conductor can extend from the first end. In various devices the accelerometer is capacitive, piezoelectric, self-powered, or externally powered and combinations thereof.

Some embodiments of the invention include a method for detecting an implantable vibrator being decoupled from a bone of the middle ear, the method including: measuring acceleration of the vibrator and using that acceleration measurement to compare to a previously measured coupled vibrator accelerometer measurement and/or comparing that measurement to a model of a freely vibrating end.

One invention embodiment provides a method for detecting an implantable vibrator coupled to a bone of the middle ear having the vibration undesirably impeded, the method including: measuring acceleration of the vibrator and using that acceleration measurement to compare to a previously measured coupled vibrator accelerometer measurement.

DETAILED DESCRIPTION

Figure 1:
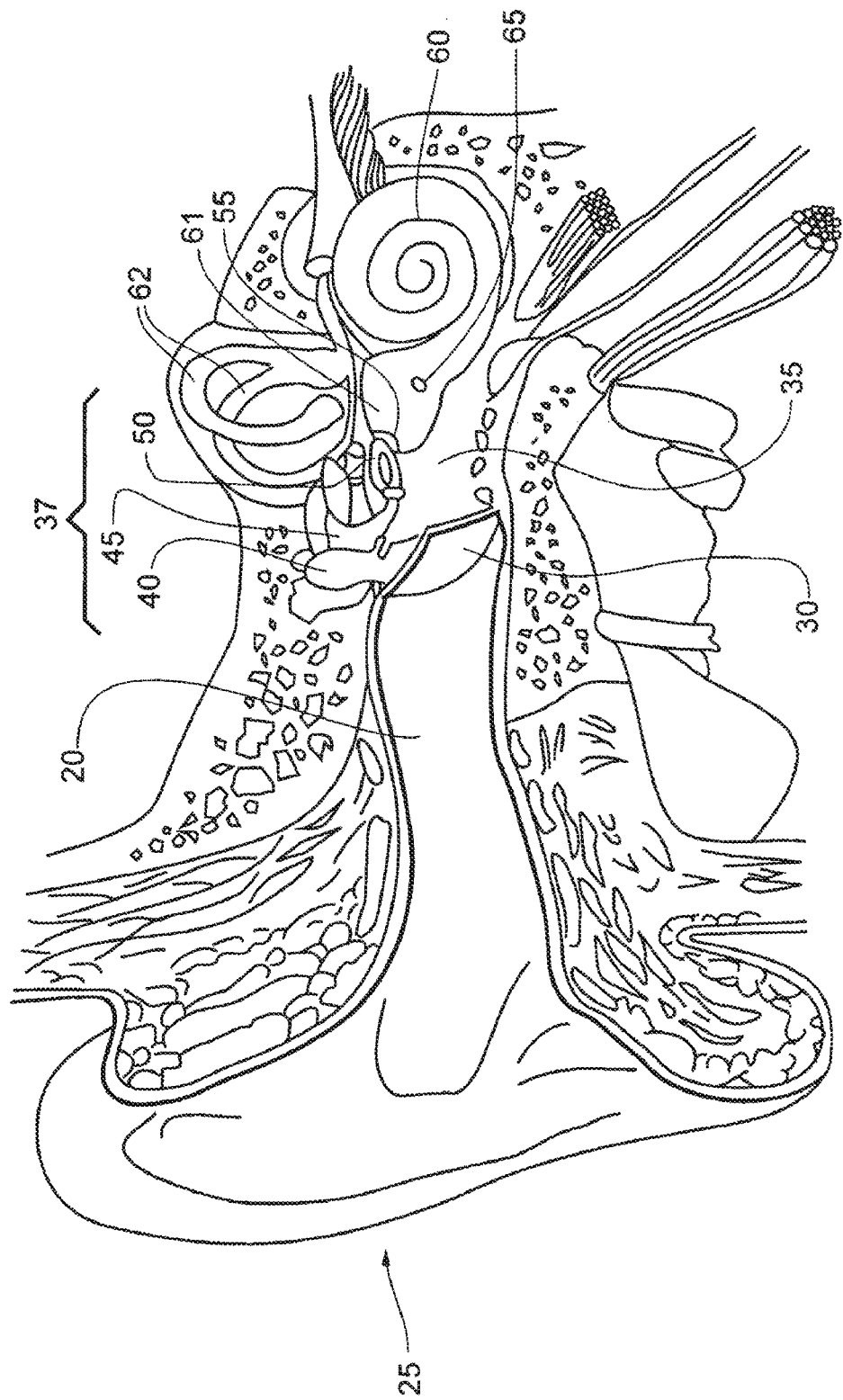
FIG. 1 illustrates a frontal section of an anatomically normal human right ear.

The following detailed description should be read with reference to the drawings, in which like elements in different drawings are numbered identically unless otherwise indicated. The drawings depict selected embodiments and are not intended to limit the scope of the invention. It will be understood that embodiments shown in the drawings and described below are merely for illustrative purposes, and are not intended to limit the scope of the invention as defined in the claims.

Some embodiments of the invention provide an electro-mechanical transducer which is particularly advantageous when used in a middle ear implantable hearing aid system, such as a partial middle ear implantable (P-MEI), total middle ear implantable (T-MEI), or other hearing aid system. A P-MEI or T-MEI hearing aid system assists the human auditory system in converting acoustic energy contained within sound waves into electrochemical signals delivered to the brain and interpreted as sound.

FIG. 1 illustrates, generally, the human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal, between it and the tympanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as the ossicular chain 37. Thus, the ossicular chain transforms acoustic energy at the eardrum to mechanical energy at the cochlea 60.

The ossicular chain 37 includes three primary components: a malleus 40, an incus 45, and a stapes 50. The malleus 40 includes manubrium and head portions. The manubrium of the malleus 40 attaches to the tympanic membrane 30. The head of the malleus 40 articulates with one end of the incus 45. The incus 45 normally couples mechanical energy from the vibrating malleus 40 to the stapes 50. The stapes 50 includes a capitulum portion, comprising a head and a neck, connected to a footplate portion by means of a support crus comprising two crura. The stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus 45 articulates the capitulum of the stapes 50 to complete the mechanical transmission path.

Normally, prior to implantation of the hearing aid system according to some embodiments of the invention, tympanic vibrations are mechanically conducted through the malleus 40, incus 45, and stapes 50, to the oval window 55. Vibrations at the oval window 55 are conducted into the fluid filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain 37, and/or cochlea 60 can disrupt or impair normal hearing.

Hearing loss due to damage in the cochlea is referred to as sensorineural hearing loss. Hearing loss due to an inability to conduct mechanical vibrations through the middle ear is referred to as conductive hearing loss. Some patients have an ossicular chain 37 lacking sufficient resiliency to transmit mechanical vibrations between the tympanis membrane 30 and the oval window 55. As a result, fluidic motion in the cochlea 60 is attenuated. Thus, receptor cells in the cochlea 60 do not receive adequate mechanical stimulation. Damaged elements of ossicular chain 37 may also interrupt transmission of mechanical vibrations between the tympanic membrane 30 and the oval window 55.

Implantable hearing aid systems have been developed, utilizing various approaches to compensate for hearing disorders. For example, cochlear implant techniques implement an inner ear hearing aid system. Cochlear implants electrically stimulate auditory nerve fibers within the cochlea 60. A typical cochlear implant system may include an external microphone, an external signal processor, and an external transmitter, as well as an implanted receiver and an implanted probe. A signal processor converts speech signals transduced by the microphone into electrical stimulation that is delivered to the cochlea 60.

A particularly interesting class of hearing aid systems includes those which are configured for disposition principally within the middle ear space 35. In middle ear implantable (MEI) hearing aids, an electrical-to-mechanical output transducer couples mechanical vibrations to the ossicular chain 37, which is optionally interrupted to allow coupling of the mechanical vibrations to the ossicular chain 37. Both electromagnetic and piezoelectric output transducers have been used to effect the mechanical vibrations upon the ossicular chain 37.

One example of a partial middle ear implantable (P-MEI) hearing aid system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus. Such electromagnetic output transducers have relatively high power consumption, which limits their usefulness in total middle ear implantable (T-MEI) hearing aid systems.

A piezoelectric output transducer is also capable of effecting mechanical vibrations to the ossicular chain 37. An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus 40, transducing mechanical energy into an electrical signal, which is amplified and further processed. A resulting electrical signal is provided to an electrical-to-mechanical piezoelectric output transducer that generates a mechanical vibration coupled to an element of the ossicular chain 37 or to the oval window 55 or round window 65. In the '366 patent, the ossicular chain 37 is interrupted by removal of the incus 45. Removal of the incus 45 prevents the mechanical vibrations delivered by the piezoelectric output transducer from mechanically feeding back to the piezoelectric input transducer.

Piezoelectric output transducers have several advantages over electromagnetic output transducers. The smaller size or volume of the piezoelectric output transducer advantageously eases implantation into the middle ear 35. The lower power consumption of the piezoelectric output transducer is particularly attractive for T-MEI hearing aid systems, which may include a limited longevity implanted battery as a power source.

A piezoelectric output transducer is typically implemented as a ceramic piezoelectric bi-element transducer, which is a cantilevered double plate ceramic element in which two opposing plates are bonded together such that they amplify a piezoelectric action in a direction normal to the bonding plane. Such a bi-element transducer vibrates according to a potential difference applied between the two bonded plates. A proximal end of such a bi-element transducer is typically cantilevered from a transducer mount which is secured to a temporal bone within the middle ear. A distal end of such a bi-element transducer couples mechanical vibrations to an ossicular element such as stapes 50.

Figure 2:
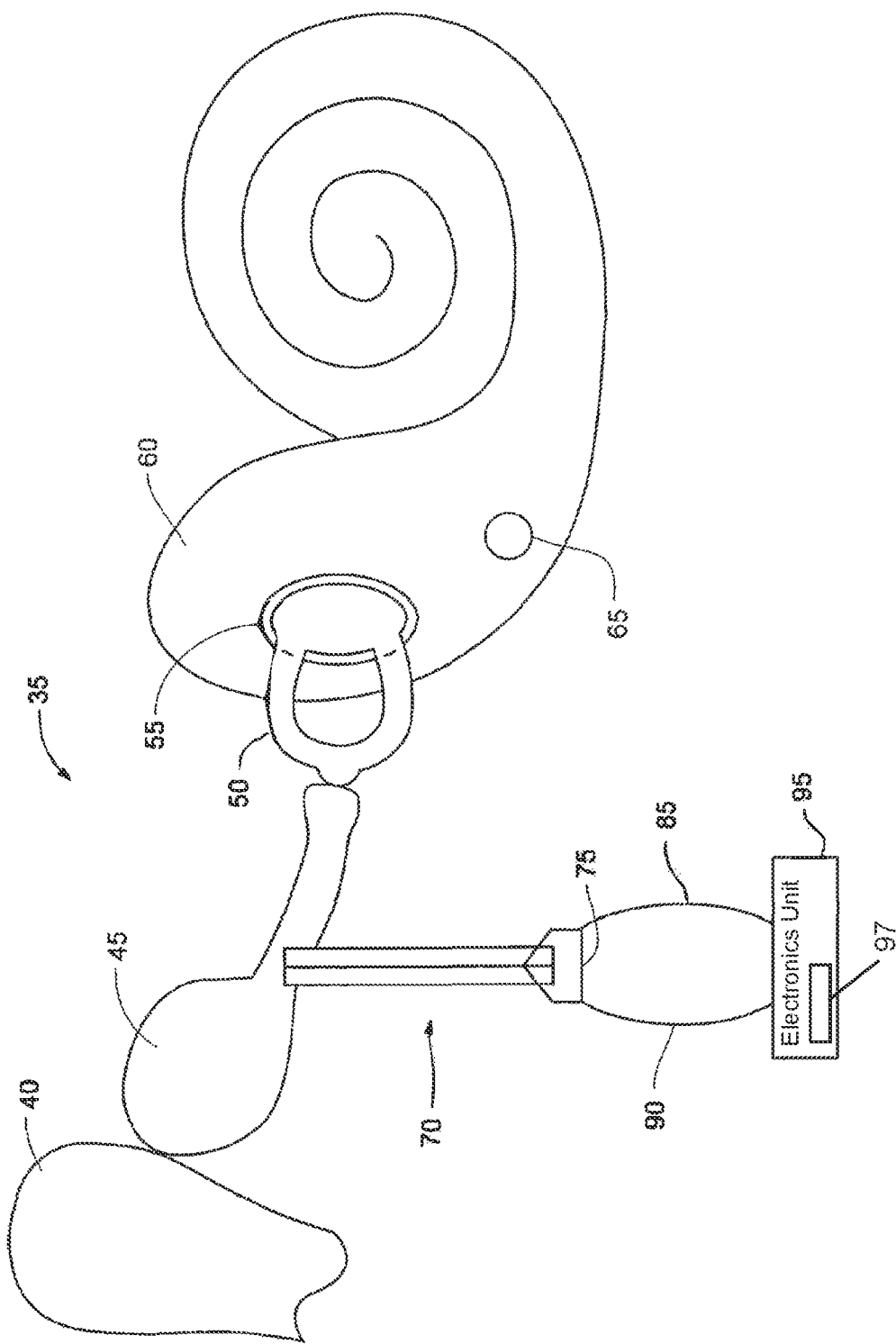
FIG. 2 is a cross-sectional illustration of a typical prior art use of a bi-element transducer coupled to an auditory element in the middle ear.

FIG. 2 is a generalized illustration of a bi-element transducer 70 cantilevered at its proximal end from a mount 75 secured to a temporal bone within middle ear 35. A distal end of bi-element transducer 70 is mechanically coupled to an auditory element to receive or effect mechanical vibrations when operating as an input or output transducer respectively. For example, to receive mechanical vibrations as an input transducer, bi-element transducer 70 may be coupled to an auditory element such as a tympanic membrane 30 (shown in FIG. 1), malleus 40, or incus 45. In another example, to effect vibrations as an output transducer, bi-element transducer 70 may be coupled to an auditory element such as incus 45, stapes 50, oval window 55, round window 65, vestibule 61 (shown in FIG. 1), or semicircular canal 62. The transducer 70 is coupled by leads 85 and 90 to an electronics unit 95, which can include embedded executable logic and/or computer code 97.

Figure 3:
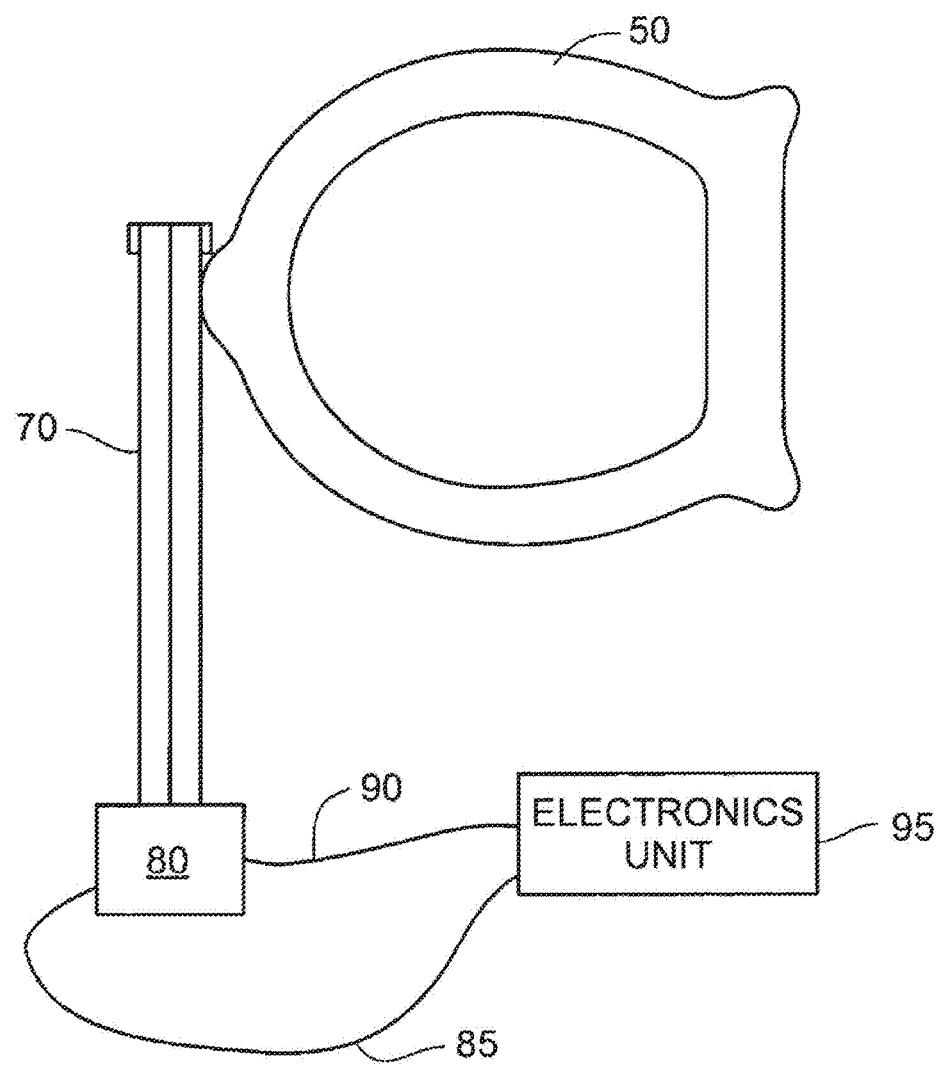
FIG. 3 is a cross-sectional illustration of a prior art bi-element transducer secured only to a vibrated auditory element.

FIG. 3 illustrates generally a cross-sectional view of an electromechanical output transducer. A piezoelectric element, more particularly bi-element transducer 70, is mechanically coupled, and preferably secured, at its proximal end to middle ear 35 (shown in FIG. 1) through an auditory element, preferably stapes 50, or alternatively incus 45, stapes 50, oval window 55, round window 65, vestibule 61, or semicircular canals 62. Bi-element transducer 70 can be secured only to stapes 50 by any known attachment technique, including biocompatible adhesives or mechanical fasteners. For example, in one embodiment, a deformable wire (not shown) secured to the proximal end of bi-element transducer 70 is looped through an inner portion of stapes 50, for example, and crimped to secure bi-element transducer 70 to stapes 50.

Electronics unit 95 may couple an electrical signal through lead wires 85 and 90 to any convenient respective connection points on respective opposing elements of bi-element transducer 70.

In response to the electrical signals received from electronics unit 95, bi-element transducer 70 bends with respect to a longitudinal plane between its opposing elements. The bending is resisted by inertial mass 80 which may be connected to bone through the use of adhesive or bone cement or a mechanical connector, for example a screw, thus mechanically coupling a force to stapes 50 through bi-element transducer 70. This force upon stapes 50 is in turn transmitted to cochlea 60 at oval window 55.

Figure 4:
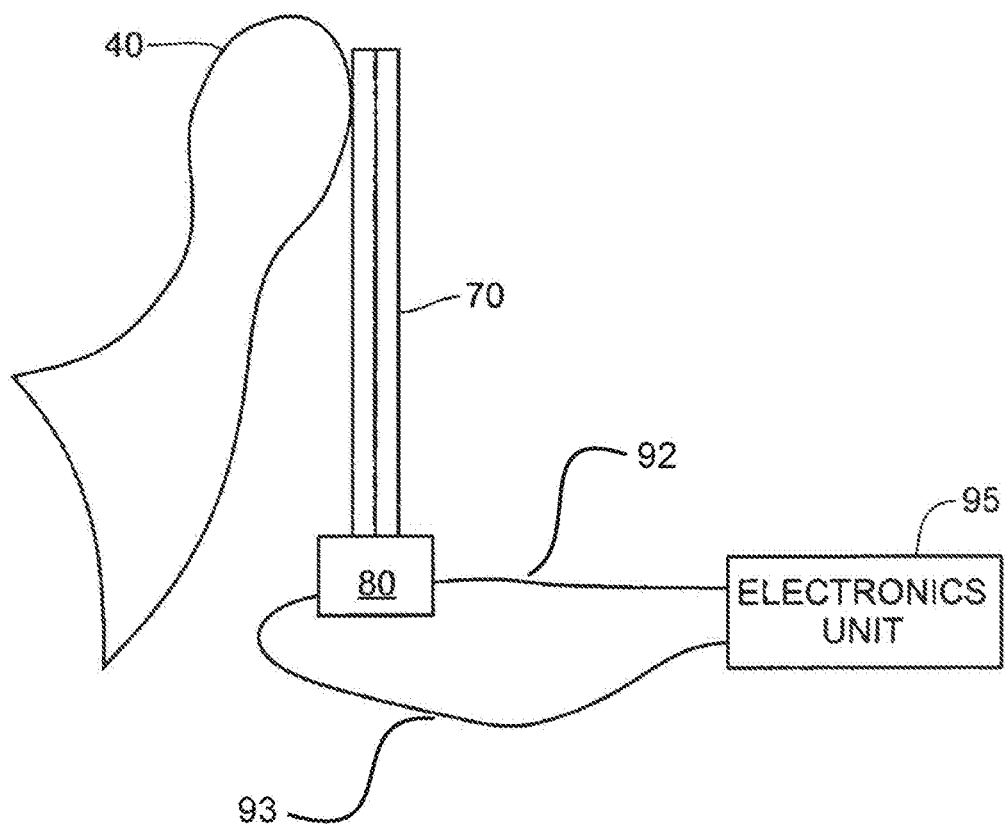
FIG. 4 is a cross-sectional illustration of a prior art bi-element transducer secured only to a vibrating auditory element.

FIG. 4 illustrates generally a cross-sectional view of an electromechanical input transducer. A piezoelectric element, such as bi-element transducer 70, is secured by any known attachment technique at its proximal end, such as described above, for example, to malleus 40.

Bi-element transducer 70 may also be secured only to other auditory elements for receiving mechanical vibrations, such as incus 45 or tympanic membrane 30. Vibrations of malleus 40 cause, at the proximal end of bi-element transducer 70, vibratory displacements that are opposed by inertial mass 80 which may be connected to bone through the use of adhesive or bone cement or a mechanical connector, for example a screw. As a result, bi-element transducer 70 bends with respect to the longitudinal plane between its opposing elements. A resulting electrical signal is provided at any convenient connection point on respective opposing elements of bi-element transducer 70, through respective lead wires 92 and 93 to electronics unit 95.

The ossicular chain can be severed at some part to break the normal sound conduction path from the ear drum (tympanic cavity), through the malleus handle through the malleus lateral process to the malleus head, then to the incus, to the incus lenticular process, to the limbs of the stapes, to the base of the stapes and to the oval (vestibular) window. In practice, the connection between the malleus and incus, or incus and stapes, can be severed, with the vibration sensor attached to the more outer portion of the severed connection and the vibrator/transducer attached to the portion of the severed connection closer to the oval window.

In previous devices, the sensor is a piezoelectric sensor and the vibrator is also a piezoelectric device. The sensor signal carries the sensed vibrations as electrical signals to the implanted medical device which can amplify the signal and the amplified electrical signal carried to the vibrator to drive the stapes or other bone to vibrate the oval window.

The proximal ends and the heads of the sensor and the transducer can both be located within a pocket carved out from the mastoid bone of the skull located behind the ear. In some current methods, both the sensor and the driver are cemented in place after securing the distal ends of the devices to the appropriate bones.

In many embodiments of the present invention, the implanted electronic device is disposed within a pocket formed in the skull by removing a portion of the skull after lifting the flap of skin. A sensor lead may extend through a channel formed along the outside of the skull and continuing to the sensor device head which continues by extending into the middle ear (tympanic) cavity. The sensor can sense the vibrations of the moving middle ear bone and transmit the vibrations as an electrical or optical signal to the implanted medical device. After processing and amplification, the transducer, driver, or vibrator lead can extend through a channel formed in the outside of the skull and be coupled to the head of the vibrator which is coupled to the vibrator body which is in turn coupled to the stapes (for example).

In various embodiments of the present invention, the sensor lead may be replaced by a different sensor lead and the driver or vibrator lead can be replaced by a different lead as well. The sensor and vibrator bodies may also be replaced with different devices. In some embodiments, the sensor and/or vibrator bodies may still be secured at the proximal region to the skull, but the exact location of the affixed bodies relative to the coupled bones may not be as critical as is currently the case.

Conceptually, an accelerometer can behave as a damped mass on a spring. When the accelerometer experiences an acceleration, the mass is displaced to the point that the spring is able to accelerate the mass at the same rate as the casing. The displacement can then be measured to give the acceleration.

In commercial devices, piezoelectric, piezoresistive and capacitive components are commonly used to convert the mechanical motion into an electrical signal. Piezoelectric accelerometers rely on piezoceramics (e.g. lead zirconate titanate) or single crystals (e.g. quartz, tourmaline). They are unmatched in terms of their upper frequency range, low packaged weight and high temperature range. Piezoresistive accelerometers are preferred in high shock applications. Capacitive accelerometers typically use a silicon micromachined sensing element. Their performance is superior in the low frequency range and they can be operated in servo mode to achieve high stability and linearity.

Modern accelerometers are often small micro electromechanical systems (MEMS), and are indeed the simplest MEMS devices possible, consisting of little more than a cantilever beam with a proof mass (also known as a seismic mass). Damping results from the residual gas sealed in the device. As long as the Q-factor is not too low, damping does not result in a lower sensitivity.

Under the influence of external accelerations the proof mass deflects from its neutral position. This deflection is measured in an analog or digital manner. Most commonly, the capacitance between a set of fixed beams and a set of beams attached to the proof mass is measured. This method is simple, reliable, and inexpensive. Integrating piezoresistors in the springs to detect spring deformation, and thus deflection, is a good alternative, although a few more process steps are needed during the fabrication sequence. For very high sensitivities quantum tunneling has been used; this requires a dedicated process making it very expensive. Optical measurement has been demonstrated on laboratory scale.

A far less common type of MEMS-based accelerometer contains a small heater at the bottom of a very small dome that heats the air inside the dome to cause it to rise. A thermocouple on the dome determines where the heated air reaches the dome and the deflection off the center is a measure of the acceleration applied to the sensor.

Most micromechanical accelerometers operate in-plane, that is, they are designed to be sensitive only to a direction in the plane of the die. By integrating two devices perpendicularly on a single die a two-axis accelerometer can be made. By adding an additional out-of-plane device three axes can be measured. Such a combination may have much lower misalignment error than three discrete models combined after packaging.

Micromechanical accelerometers are available in a wide variety of measuring ranges, reaching up to thousands of g's. The designer must often make a compromise between sensitivity and the maximum acceleration that can be measured.

Various accelerometers can include various technologies such as piezoelectric accelerometers, shear mode accelerometers, surface micromachined capacitive (MEMS), thermal (submicron CMOS process), bulk micromachined capacitive, bulk micromachined piezoresistive, capacitive spring mass base electromechanical servo (servo force balance), null-balance, strain gauge, resonance, magnetic induction, optical, surface acoustic wave (SAW), laser accelerometer, DC response, high temperature, low frequency, high gravity, triaxial, modally tuned impact hammers, seat pad accelerometers, and pendulous integrating gyroscopic accelerometer.

Accelerometers can include capacitive metal beam or micromachined devices which produce change in capacitance related to acceleration; piezoelectric crystal mounted to mass having a voltage output converted to acceleration; piezoresistive having a beam or micromachined feature whose resistance changes with acceleration; a Hall Effect motion device producing an electrical signal by sensing of changing magnetic fields; a magnetoresistive device having material resistivity changes in the presence of a magnetic field.

The degree of vibration can be used also to determine whether the vibratory body is effectively coupled to the middle bone at the time of the initial surgery. This can be done as the vibratory behavior of the vibratory body will be different if the body is freely vibrating as opposed to being coupled to and driving the middle ear bone.

At a time long after the initial surgical implantation the vibratory behavior of the bimorph can be compared with the initial behavior. One change could be the decoupling of the driven bimorph from the middle ear bone. Another change could be added vibratory impedance or impediment to vibration. This impediment could be scar tissue, fluid, disease, unwanted growths, and the like. Significant changes could be signaled to the patient and/or to medical professionals.

Figure 5:
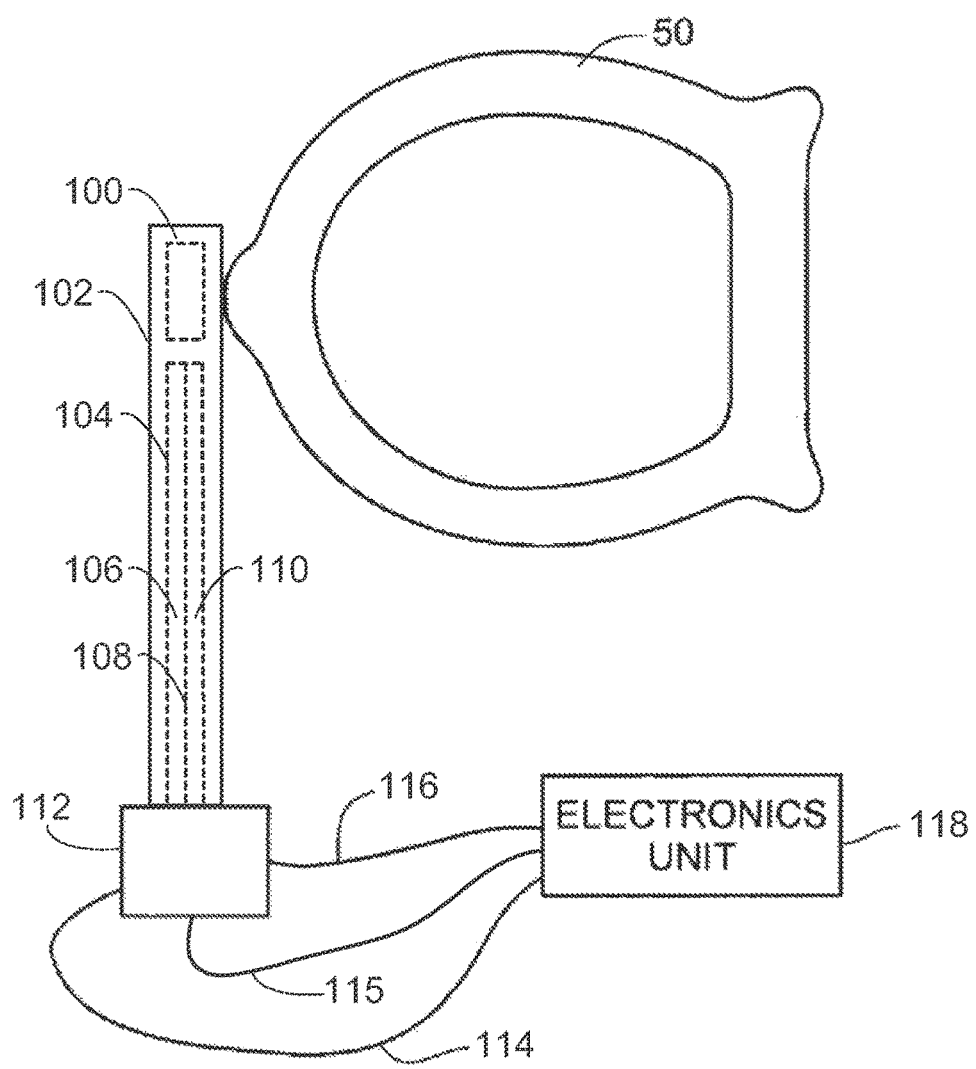
FIG. 5 is a schematic drawing of a bi-element transducer having an accelerometer included in the distal tip.

FIG. 5 illustrates one embodiment of the invention having a hermetically sealed elongate housing or vibratory body 102 having an accelerometer 100 included in the distal tip. The distal tip is secured to a bone of the middle ear, in this case, stapes 50. A proximal end 112 of body 102 is shown, which can be used to anchor body 102 to a body region near the middle ear, for example, part of the skull. In this example, body 102 has a bi-element piezoelectric transducer to impart vibrations to the stapes. Bi-element 104 includes a first piezoelectric body 106, a second piezoelectric body 110, and a metallic center vane 108 disposed between bodies 106 and 110.

Three wires are shown extending from the proximal end 112 to the electronics unit 118. In this example, wire 114 is used to drive the piezoelectric transducer 104 and wire 115 is used to return sensor data from accelerometer 100. Wire 116 serves as a common ground, shared by piezo electric transducer 104 and accelerometer 100. In another embodiment, the transducer 104 and the accelerometer 100 could each have a separate ground wire 116.

In some embodiments, the accelerometer is self powered, not requiring any externally wired power source. One example of this is a piezoelectric accelerometer, which generates its own electrical potential or charge as it moves. The charge generated can then be coupled directly or indirectly to the electronics unit 118. In one example, the electrical potential is converted to light and transmitted to the electronics unit 118 via a fiber optic conduit.

Figure 6:
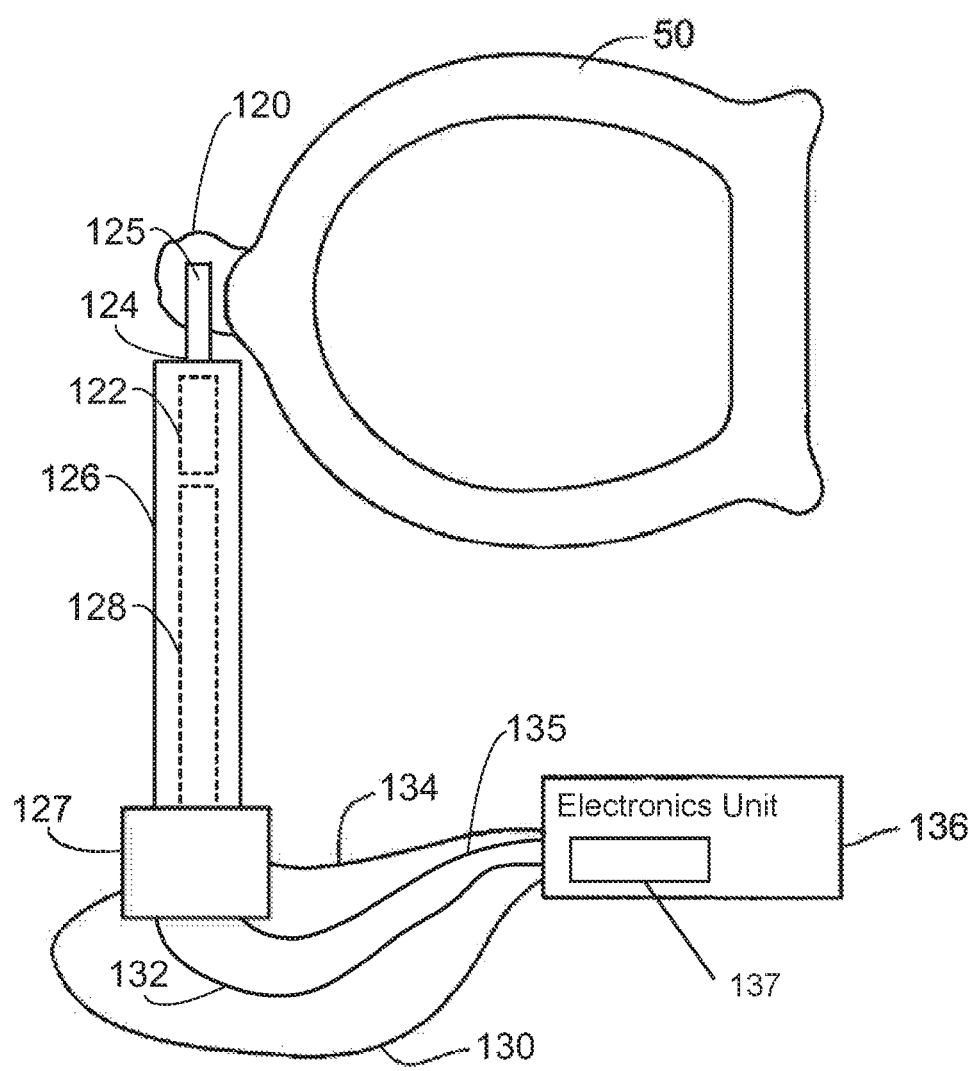
FIG. 6 is schematic drawing of a bi-element transducer having an accelerometer included in the distal region.

FIG. 6 illustrates another embodiment of the invention having vibratory body 126 with a distal region 124 and a distal tip 125 coupled to a stapes 50 using adhesive or cement 120. An accelerometer 122 is disposed in the vibratory body 126 in the distal region 124 distant from the distal tip 125. The acceleration measured may be different than the acceleration at the distal tip. The acceleration at the distal tip can be calculated using the known geometry of the vibratory body, in particular the distance of accelerometer 122 from the distal tip.

Some accelerometers, for example capacitive accelerometers, are not self-powered and require an externally wired power source. In this example, four wires couple elongate body proximal end 127 to an electronics unit 136, which can include embedded executable logic and/or computer code 137. Wire 130 can be used to drive bi-element 128 while wire 132 can be used to power accelerometer 122. Wire 134 can be used to return acceleration data from accelerometer 122 and wire 135 can serve as a common ground. In another embodiment, the bi-element 128 and the accelerometer 122 could each have a separate ground wire 135.

The accelerometer data obtained can be used as an indication of actual acceleration of the vibratory body. Velocity is the rate of change of position of an object, the first derivative of the position. Acceleration is the rate of change of the velocity, the second derivative of the position. Acceleration can be integrated to obtain the velocity and velocity can be integrated to determine the displacement or actual motion of the accelerometer. For these reasons, the acceleration waveform can be used itself as an indication of the motion of the middle ear element such as an incus, stapes, or a transducer. Therefore, a change in acceleration at the same frequency over time is indicative of changes in the implanted system, for example, decoupling of the vibratory body from the middle bone, fluid accumulation, scar tissue, and the like.

What is claimed is:

1. An implantable middle ear transducer device comprising:

an elongate housing having a first end and a second end, the first end configured to fixedly secure to a body region, the second end configured to couple to an auditory element, the elongate housing comprising:
- a piezoelectric transducer coupled to the elongate housing and configured to impart vibrations into the auditory element; and
- an accelerometer secured to the second end of the elongate housing and configured to measure acceleration of the second end of the elongate housing.

2. The device of claim 1, wherein the body region comprises a skull temporal bone within a middle ear.

3. The device of claim 1, wherein the auditory element comprises a middle ear ossicle bone.

4. The device of claim 3, wherein the middle ear ossicle bone comprises a stapes.

5. The device of claim 1, further comprising a conductor in communication with the elongate housing for communicating information to a location outside of the elongate housing, the conductor comprising an electrical conductor or an optical conductor.

6. The device of claim 1, further comprising an implantable electronic device in communication with the elongate housing to receive information from the accelerometer.

7. The device of claim 1, wherein the accelerometer is self-powered.

8. An implantable middle ear transducer device comprising:
- an elongate housing having a proximal region and a distal region, the proximal region configured to fixedly secure to a body region, the distal region comprising:
  - a distal tip configured to couple to an auditory element; and
  - an accelerometer configured to measure acceleration of the distal region of the elongate housing;
- the elongate housing comprising a transducer coupled to the elongate housing and configured to impart vibrations into the auditory element via the distal tip.

9. The device of claim 8, wherein the body region comprises a skull temporal bone within a middle ear.

10. The device of claim 8, wherein the auditory element comprises a middle ear ossicle bone.

11. The device of claim 10, wherein the distal tip is configured to be coupled to the middle ear ossicle bone using an adhesive.

12. The device of claim 8, wherein the transducer comprises a piezoelectric bi-element transducer.

13. The device of claim 8, further comprising an implantable electronic device in communication with the elongate housing and configured to receive information from the accelerometer.

14. The device of claim 13, wherein the implantable electronic device comprises embedded executable logic and/or computer code to calculate the acceleration of the distal tip using the acceleration of the distal region measured by the accelerometer and geometry of the elongate housing.

15. The device of claim 13, wherein the implantable electronic device comprises embedded executable logic and/or computer code for detecting excessively impeded vibration of the elongate housing.

16. A method for sensing vibrational driving of an auditory element by a vibrational device coupled to the auditory element, the method comprising:
- securing a proximal end of the vibrational device to a body region;
- coupling a distal end of the vibrational device to the auditory element, the distal end of the vibrational device comprising an accelerometer configured to measure acceleration of the distal end;
- driving the vibrational device to vibrate the auditory element via the distal end; and
- measuring a signal indicative of the acceleration of the distal end of the vibrational device using the accelerometer.

17. The method of claim 16, wherein the auditory element comprises a middle ear bone.

18. The method of claim 16, wherein the body region comprises a skull temporal bone within a middle ear.

19. The method of claim 16, wherein the distal end of the vibrational device comprises a distal tip and wherein coupling the distal end to the auditory element comprises coupling the distal tip to the auditory element.

20. The method of claim 19, further comprising calculating the acceleration of the distal tip using the signal indicative of the acceleration of the distal end and geometry of the vibrational device.

* * * * *